United States Patent [19]

Frey et al.

[11] Patent Number: 4,560,463

[45] Date of Patent: Dec. 24, 1985

[54] GAS SENSOR, PARTICULARLY OXYGEN SENSOR EXPOSED TO COMBUSTION EXHAUST GASES

[75] Inventors: Thomas Frey, Friolzheim; Werner Grünwald, Gerlingen; Günther Knoll, Stuttgart; Helmut Weyl, Schwieberdingen, all of Fed. Rep. of Germany

[73] Assignee: Robert Bosch GmbH, Stuttgart, Fed. Rep. of Germany

[21] Appl. No.: 632,584

[22] Filed: Jul. 19, 1984

[30] Foreign Application Priority Data

Aug. 3, 1983 [DE] Fed. Rep. of Germany ....... 3327991

[51] Int. Cl.⁴ .......................................... G01N 27/46
[52] U.S. Cl. ................................... 204/424; 204/427; 204/428; 219/523; 219/543; 219/553
[58] Field of Search ................................. 204/421–429; 219/270, 523, 543, 553

[56] References Cited

U.S. PATENT DOCUMENTS

| | | |
|---|---|---|
| 2,030,937 | 2/1936 | Reichmann ......................... 219/270 |
| 4,035,613 | 7/1977 | Sagawa et al. . |
| 4,155,827 | 5/1979 | Maurer et al. ...................... 204/428 |
| 4,169,778 | 10/1979 | Mann et al. ........................ 204/429 |
| 4,219,399 | 8/1980 | Gruner et al. ...................... 204/428 |
| 4,357,526 | 11/1982 | Yamamoto et al. ................ 219/553 |
| 4,437,971 | 3/1984 | Csanitz et al. ..................... 204/428 |

FOREIGN PATENT DOCUMENTS

| | | | |
|---|---|---|---|
| 0056837 | 8/1982 | European Pat. Off. ............ | 204/428 |
| 8101584 | 6/1981 | Fed. Rep. of Germany . | |

Primary Examiner—T. Tung
Attorney, Agent, or Firm—Frishauf, Holtz, Goodman & Woodward

[57] ABSTRACT

A rod-like electrical heating element is incorporated in the interior of a tubular solid electrolyte sensor connecting zones of the heating element are disposed on the end face thereof remote from the sensing end. Electrical connecting parts are pressed against the connecting zones of the heating element by means of a spring element. These electrical connecting parts are in electrical contact with the connecting cable of the gas sensor via conductor wires, leads or other connecting means.

13 Claims, 2 Drawing Figures

GAS SENSOR, PARTICULARLY OXYGEN SENSOR EXPOSED TO COMBUSTION EXHAUST GASES

The present invention relates to an gas sensor, and more particularly to an oxygen sensor to determine the oxygen content in exhaust gases from a combustion process, especially the exhaust gases from an internal combustion engine.

BACKGROUND

Various types of gas sensors have been proposed; see for example U.S. Pat. No. 4,155,827, MAURER et al., assigned to the assignee of the present invention, in which a tubular solid electrolyte is closed at one end, the outside of the solid tubular electrolyte being exposed to the exhaust gases and the inside to ambient air, to provide a reference oxygen level. The sensor is enclosed in a tubular metal housing, which may be a two-part structure, and electrodes are applied to the inner surface as well as to the outer surface of the solid electrolyte tubular body. To provide for uniformity of output measurement, the solid electrolyte body should be operated at an essentially unvarying temperature. During start-up, and before exhaust gases, e.g. from an internal combustion engine (ICE), have reached a predetermined temperature level, a heater element is energized to raise the temperature of the solid electrolyte body to an operating temperature, for example above 250° C. or 300° C. Upon subsequent continued operation of the ICE, the temperature of the solid electrolyte sensing element can be maintained due to the heat of the exhaust gases.

To raise the temperature, it has previously been proposed to introduce a heater element into the interior region of the solid electrolyte body (see the referenced U.S. Pat. No. 4,155,827). The heater element may be a rod-like electrical structure. Assembling such a heater element within the interior of the solid electrolyte tubular body is complicated, and hence expensive.

Heating elements having heating coils applied to their surface by printing or similar technology and which are covered by means of thin electrical-insulating layers are already known from the referenced U.S. Pat. No. 4,035,613.

THE INVENTION

It is anobject to simplify the structure of a heated oxygen sensor of the solid electrolyte type so that it can be readily assembled and, hence, manufactured at a lower cost.

Briefly, a rod-like elongated heating element is formed with a flange-like or plug-like end portion which is located, typically, within the region of the housing. The flange-like end portion has a top surface, that is, a surface facing the measuring end of the sensor, and areal connecting zones are formed on the flange-like or plug-like end portion. These areal connecting zones extend in the form of layer-like electrodes around the flange or plug-like portion, so that, at the region where the flange or plug-like portion merges into the rod portion of the heating element, they can form connections to, or directly embody, heater connections or connecting regions for an electrode of the solid electrolyte body, for example. The layer-like electrodes which extend around the flange or plug-like portion are then connected, at the upper, flat surface, to a connecting lead, for instance in the form of a wire, but it may be a connective track, which passes through an insulating structure which is maintained in resiliently compressed state, for example by a spring washer, against the flange or plug-like portion. Thus, all elements of the structure can be assembled, in sequence, by placing one tubular element after another within the tubular housing, without requiring special connections within the housing or any complicated assembly steps.

The sensor has the advantage that the inner structure is simple, thus permitting substantially simplified, and hence faster and cheaper, assembly. Additionally, the structure is more resistant to vibration and shock than prior art structures, a feature which is particularly important when the sensor is to be used as an exhaust gas sensor in the exhaust system of an automotive ICE installed in vehicle.

In accordance with a particularly preferred form of the invention, the various elements are retained axially by axial compressive force under the action of a dish or cup spring, the cup spring at the same time providing for resilient engagement of the elements with each other, thereby avoiding transmission of shocks and vibration from a vehicle or the engine, for example, directly to the solid electrolyte body—which, typically, is zirconium dioxide and hence brittle and subject to fracture—while also providing for excellent electrical connection of the respective conductive tracks and/or wires, thereby permitting elimination of solder joints and the like which are difficult to carry out in the tiny structures involved.

DRAWING

FIG. 1 is a longitudinal section taken through a gas sensor according to the invention, shown larger than actual size; and FIG. 2 is a perspective view, on an even larger scale, of the heating element (without the electrical insulating layer) of the gas sensor according to FIG. 1.

DETAILED DESCRIPTION

Figure 1:
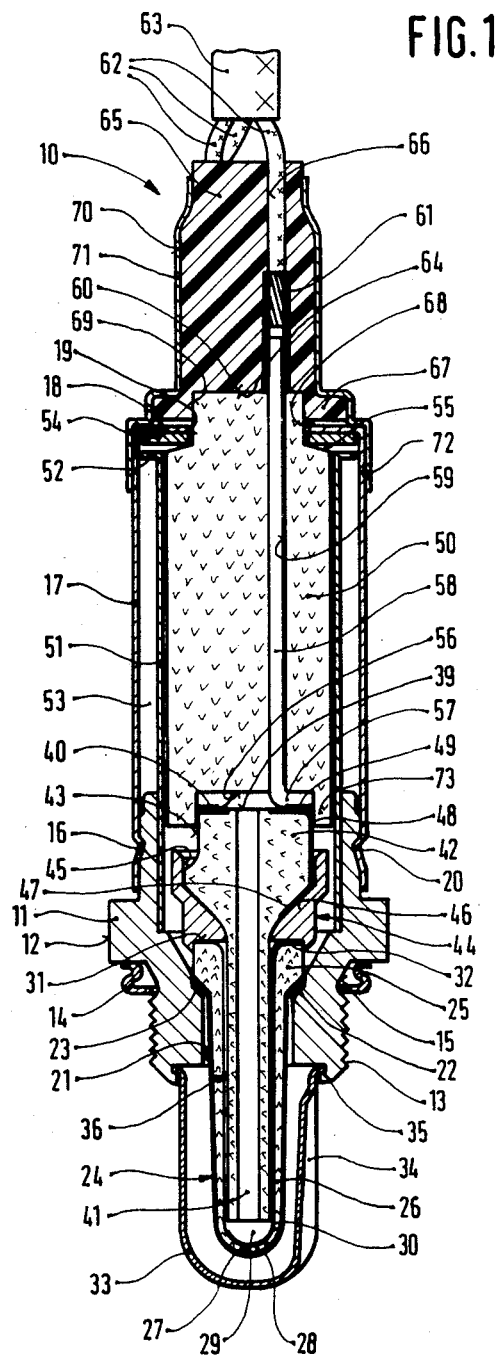
Figure 2:
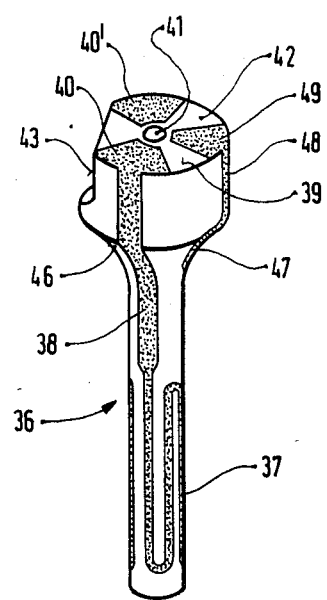

The gas sensor 10 shown in FIGS. 1 and 2 has an elongated tubular metal housing 11, which has a hexagonal nut 12 on its outside and a thread 13, as means for securing it when installed in a pipe (not shown) carrying gas to be measured; so that this housing 11 can be installed in a sealing manner in the pipe carrying the gas to be measured, there is an annular sealing element 14, which is captively fixed in an annular groove 15 disposed between the hexagonal nut 12 and the thread 13. A further annular groove 16 is cut into the part of the housing 11 remote from the measuring gas, that is, at the connecting end portion of the housing 11 and serves to fix a closure sleeve 17 which extends the length of the housing 11. This closure sleeve 17, which remote from the gas to be measured has a bottom 18 with a central opening 19, is fixed in the annular groove 16 by means of a plurality of crimpings 20.

The housing 11 has a longitudinal bore 21 with a shoulder 22, which faces away from the measuring side of the gas sensor 10 and bears an annular sealing element 23. With its head 25, a sensor element 24 rests on this shoulder 22 of the longitudinal housing bore 21 that bears the sealing element 23.

This sensor element 24, in the present example, is an oxygen sensor known per se, as described in German Utility Model DE-Gmb S No. 81 01 584, and is preferably used for measuring the partial pressure of the oxygen in the exhaust gases of internal combustion engines. This sensor element 24 has a tubular solid electrolyte sensing element 26, the sensing end portion of which is closed off by a bottom 27. On its outer or sensing end exposed to the gas to be measured, this solid electrolyte sensing element 26 has a layer-like, gas-pervious measuring electrode 28, and on its end toward the interior 29, it has a layer-like, gas-pervious reference electrode 30 which is exposed to a reference gas (for instance, air). While the measuring electrode 28 is in mechanical contact with the electrically grounded housing 11, the reference electrode 30 preferably leads from the inside of the bottom 27 as far as the end face 31 of the solid electrolyte element 26 remote from the measuring gas, or in other words on the end side. The areal connecting region of the reference electrode 30 on the end face 31 of the solid electrolyte element 26 is shown at 32. To prolong the service life of the measuring electrode 28, which typically comprises a thin layer of platinum, this electrode 28 is coated with a gas-pervious (not shown) protective layer, which may for instance be made of magnesium spinel.

The portion of the sensor element 24 protruding out of the longitudinal bore 21 of the housing 11 on the sensing end is surrounded at a distance by a protective tube 33, which has openings 34 for the inflow and outflow of gases to be measured, and is secured on the end of the housing 11 toward the gas to be measured by a flange 35 or some other means. This protective tube 33 serves to prevent severe temperature changes and particles contained in the measuring gas from affecting the sensor element 24 and damaging it.

The interior 29 of the sensor element 24 is substantially filled up by a rod-like electrical heating element 36, which also protrudes out from the interior 29 of the sensor element 24 on the end remote from the measuring gas. This elongated electrical heating element 36 has heating coils 37 on its sensing end in the form of conductive tracks, which comprise some suitable material (for instance, platinum or tungsten) and which assure that the portion of the sensor element 24 protruding out from the housing 11 and serving to perform the actual measurement is heated thereby.

According to a feature of the invention, these heating coils 37 are in electrical contact with the end surface 39 remote from the measuring gas via conductive tracks 38 and here form areal connecting zones 40 and 40' which are electrically separated from one another. The heating coils 37 and the conductive tracks 38 are covered by a thin electrical insulation (not shown), which may for example comprise aluminum oxide. This heating element 36 is furthermore provided with an axial bore 41, which facilitates the inflow of the reference gas, or air, to the reference electrode 30 of the sensor element 24, and on its end remote from the measuring gas it has a head 42 with a lateral fixation surface 43. The carrier material for the heating element 36 is preferably a ceramic, such as aluminum oxide.

An annular connecting element 44 which is electrically conductive and coaxially surrounds the heating element 36 below its head 42 rests on the end face 31 of the sensor element 24 remote from the measuring gas. The central bore 45 of the electrical connecting element 44 is adapted in shape to the plug-like end portion 46 on the sensing end of the heating element head 42. By means of this electrical connecting element 44, an electrically connection between the areal connecting region 32 of the reference electrode 30 and a first connecting zone 47 on the end portion 46 of the heating element head 42 is established; this first connecting zone 47 is areal in embodiment and may for example be formed by a layer of platinum. From this first areal connecting zone 47, a conductive track 48 leads as far as the end surface 39 remote from the measuring gas of the heating element 36 and there forms a second areal connecting zone 49; this second areal connecting zone 49 remains spaced apart from the connecting regions 40 and 40', which are electrically connected with the heating coils 37 via conductive tracks 38. The conductive track 48 which joins the first areal connecting zone 47 with the second areal connecting zone 49 may be covered with a thin electrical insulating layer of some known material (for instance, aluminum oxide).

An insulating part 50, which is preferably of some ceramic material (such as aluminum oxide), is accommodated in the chamber that is substantially defined by the end face 39 of the heating element 36 remote from the measuring gas, the housing 11 and the closure sleeve 17, and it is held coaxially in the gas sensor 10 by means of a guide sleeve 51. This guide sleeve 51 is secured in the longitudinal bore of the housing 11 (by crimping, bracing or soldering, for instance), on its end toward the measuring gas, and on its end remote from the measuring gas it has a flange 52 that points outward and extends laterally approximately as far as the closure sleeve 17. The annular chamber 53 formed between this guide sleeve 51 and the closure sleeve 17 acts as a barrier to moisture that can enter the gas sensor 10, in the region between the end of the closure sleeve 17 toward the measuring gas and the housing 11, along with the air serving as the reference gas. An annular spring element 54 (dish spring) is disposed between the flange 52 of the guide sleeve 51 and the bottom 18 of the closure sleeve 17 and is supported at one end on the bottom 18 of the closure sleeve 17, while on the other end it rests with mechanical bias on a coaxial shoulder 55 of the insulating part 50 oriented away from the measuring end of the gas sensor 10. Because of the mechanical biasing of the spring element 54, the insulating part 50 is pressed with its end face 56 oriented toward the gas sensing end in the direction of the end surface 39 of the heating element 36 remote from the gas to be measured; as a result, it presses a respective electrical connecting part 57 against each of the three areal connecting zones 40, 40' and 49 on the end surface 39 of the heating element 36 nearer the measuring gas. These electrical connecting parts 57 are embodied by end portions, bent over in a preferred manner, of connecting means, preferably in the form of wires 58, which extend in and along longitudinal bores 59 in the insulating part 50. The end portions of these connecting means 58 which are remote from the measuring gas protrude a short distance out from the insulating part 50 on the end remote from the measuring gas; the end face of the insulating part 50 remote from the measuring gas is indicated at 60. One connecting sleeve 61 is placed over each end portion of a connecting means 58 that protrudes out from the insulating part 50 on the end remote from the measuring gas and is fixed in place by some known method (for instance, deforming, crimping, soldering or welding). Since the connecting sleeves 61, on their ends toward the measuring gas, rest on the end face 60, the connecting means 58 are fixed with their electrical connecting parts 57 in the insulating part 50. The ends of the connecting sleeves 61 remote from the measuring gas encompass the bared end portions of the connecting wires 62 of a connecting cable 63. The bared end portions of the connecting wires 62 on the end toward the measuring gas are secured in the connecting sleeves 61 by crimping, welding and/or soldering.

Also resting on the end face 60 of the insulating part 50 remote from the measuring gas, in addition to the connecting sleeves 61, is the end face 64 oriented toward the measuring gas of an elastic insulating plug 65, through the longitudinally extending through bores 66 of which the connecting wires 62, including the connecting sleeves 61, pass in a sealed manner, On the end toward the measuring gas this insulating plug 65 is equipped with a flange part 67, the end face 68 of which, facing toward the measuring gas, rests in a sealing manner on the outside of the closure sleeve bottom 18. The end face 64 of the insulating plug 65 toward the measuring gas is disposed in a preferred manner in a coaxial recess 69 in the flange part 67, which receives the end portion of the insulating part 50 that is remote from the gas to be measured. A tubular, preferably metallic head sleeve 71 is disposed on the jacket face 70 of this insulating plug 65 and with its enlarged end portion toward the measuring gas it tightly grips the end portion of the closure sleeve 17 remote from the measuring gas; it is fixed on this closure sleeve 17 by means of a plurality of spot welds 72 or other known securing means and it holds the insulating plug 65 with mechanical biasing in the longitudinal direction of the gas sensor 10.

In order to assure correct positioning between the connecting zones 40, 40' and 49 on the end face 39 remote from the measuring gas of the heating element 36 and the electrical connecting parts 57 together with their connecting leads 58, an annular protrusion 73 is integrally formed on the end face 56 on the measuring end of the insulating element; this annular protrusion 73 laterally encompasses a portion of the head 42 of the heating element and also, in order to attain positionally correct assembly, rests on the fixation surface 43 of the heating element head 42. At least one of the electrical connecting parts 57 may additionally be disposed in a groove or depression (not shown) in the heating element end surface 39 remote from the measuring gas, and optionally in the insulating part end face 56 toward the measuring gas as well, thus also serving the purpose of fixation.

In particular forms of embodiment of the gas sensor 10 described, the connecting element 44 can be omitted; in that case the connecting regions 32 and 47 are preferably embodied somewhat larger and/or thicker than in the gas sensor 10 described above.

We claim:

1. Gas sensor, particularly to determine oxygen content in combustion exhaust gases, especially from an internal combustion engine having
    an elongated tubular housing (11, 17) defining a sensing end portion and a connecting end portion of the sensor;
    a tubular solid electrolyte sensing element (26), closed at the sensing end portion located at the sensing end portion of the housing and secured therein, and having layer electrodes (28, 30) thereon extending over, respectively, an outer and an inner surface thereof;
    An electrical heating element (36) located within the tubular solid electrolyte element having a layer heater means (37) terminating in two heater connecting zones (40, 40'), said heater element (36) comprising an elongated rod portion and a flange end portion,
    said layer heater means extending on the rod portion,
    said flange end portion having a diameter larger than the diameter of the elongated rod portion, being located at the end remote from the closed end of the tubular electrolyte, and having an end face (39) facing the connecting end portion of the sensor,
    said heater connecting zones (40, 40') being located on said end face (39),
    a plurality of electrically conductive tracks (38, 48) formed on said heater element, a first (48) of said tracks being in electrical contact with that one (30) of the layer electrodes of the sensing element at the inner surface of the sensing element and extending to a connecting zone (49) on the end face (39) of the heater element, and
    a second (38) and a third (38) of said tracks connecting said heater means with the heater connecting zones (40, 40') on the end face (39) of the heater element,
    and electrical connection means (58) extending within the housing and in electrical contact with the respective electrically conductive connection portions and leading to the terminal end of the connecting portion of the sensor.

2. Sensor according to claim 1, wherein the electrical connection means (58) comprise connecting wires in pressure-engagement with the respective connecting zones (40, 40', 49) at the end surface (39) of the flange end portion (46).

3. Sensor according to claim 1, wherein the connecting zones (40, 40', 49) are located substantially in the same plane.

4. Sensor according to claim 3, including electrical connecting parts (57) which are in electrical contact with the connection means (58) and rest firmly on the connecting zones (40, 40', 49).

5. Sensor according to claim 4, including a spring element (54) pressing the electrical connecting parts (57) against the connecting zones (40, 40', 49), and an electrical insulating part (50) disposed between the spring element (54) and the electrical connecting parts (57).

6. Sensor according to claim 5, wherein the insulating part (50) has longitudinally extending bores (59), through which the electrical connecting means (58) extend.

7. Sensor according to claim 5, wherein the spring element (54) rests with one end on the inside (18) of the housing in a position adjacent the connecting end portion of the sensor and with the other end on a shoulder (55) of the insulating part (50) to subject the insulating part to mechanical bias.

8. Sensor according to claim 1, including an electrical connecting element (44) located between a connecting region (32) of said one layer electrode (30) on the sensor element (24) and the first (48) of said tracks on the heating element (36) and encompassing the heating element (36), wherein the electrical connecting element (44) is electrically insulated with respect to the other tracks (38) and the heater connecting zones (40, 40') of the heating element (36).

9. Sensor according to claim 1, wherein the electrical heating element (36) has an axially extending duct (41).

10. Sensor according to claim 9, wherein the duct (41) is a through-bore.

11. Sensor according to claim 1, wherein the layer electrodes comprise a gas-pervious measuring electrode (28) exposed to the gas to be measured; and a gas-pervious reference electrode (30) exposed to a reference gas located in the inside of the sensing element (26), and wherein the tubular solid electrolyte sensing element (26) in its interior (29) retains the rod portion of the heating element (36).

12. Sensor according to claim 1, including spring means (54) resiliently pressing the electrical connection means (58) in surface contact against the respective connecting zones (40, 40', 49).

13. Sensor according to claim 12, wherein the electrical connection means (58) comprises wire elements, and the spring means (54) comprises a cup spring.

* * * * *